US008182807B2

(12) United States Patent
Labhasetwar et al.

(10) Patent No.: US 8,182,807 B2
(45) Date of Patent: May 22, 2012

(54) METHOD FOR INHIBITING REPERFUSION INJURY IN THE BRAIN

(75) Inventors: Vinod D. Labhasetwar, Omaha, NE (US); Maram K. Reddy, Omaha, NE (US)

(73) Assignee: Board of Regents of the University of Nebraska by and on Behalf of the University of Nebraska Medical Center, Omaha, NE (US)

( * ) Notice: Subject to any disclaimer, the term of this patent is extended or adjusted under 35 U.S.C. 154(b) by 1007 days.

(21) Appl. No.: 12/033,353

(22) Filed: Feb. 19, 2008

(65) Prior Publication Data

US 2008/0248118 A1    Oct. 9, 2008

Related U.S. Application Data

(62) Division of application No. 10/955,739, filed on Sep. 30, 2004, now Pat. No. 7,332,159.

(51) Int. Cl.
*A61K 38/44* (2006.01)

(52) U.S. Cl. ....... 424/94.4; 977/904; 977/905; 977/906; 424/489

(58) Field of Classification Search ............... None
See application file for complete search history.

(56) References Cited

U.S. PATENT DOCUMENTS

| | | | |
|---|---|---|---|
| 5,714,362 A | | 2/1998 | Groner |
| 5,827,222 A | * | 10/1998 | Klatz et al. ............. 604/507 |
| 5,962,566 A | | 10/1999 | Grandfils et al. |
| 5,994,339 A | | 11/1999 | Crapo et al. |
| 6,123,956 A | | 9/2000 | Baker et al. |
| 6,231,853 B1 | | 5/2001 | Hillman et al. |
| 6,254,890 B1 | | 7/2001 | Hirosue et al. |
| 6,262,279 B1 | | 7/2001 | Hyatt |
| 6,369,106 B1 | * | 4/2002 | Atlas et al. ............. 514/547 |
| 6,410,290 B1 | | 6/2002 | Robertson et al. |
| 6,429,356 B1 | | 8/2002 | Shewmaker |
| 6,436,362 B1 | | 8/2002 | Cuzzato |
| RE38,009 E | | 2/2003 | Garnett et al. |
| 6,623,743 B1 | | 9/2003 | Nair et al. |
| 6,653,530 B1 | | 11/2003 | Shewmaker et al. |
| 6,656,358 B2 | | 12/2003 | May et al. |
| 6,660,320 B1 | | 12/2003 | Pegg et al. |
| 6,730,302 B1 | | 5/2004 | Fujihara et al. |
| 6,737,552 B1 | | 5/2004 | Crombie |
| 7,332,159 B2 | | 2/2008 | Labhasetwar et al. |
| 2005/0255152 A1 | | 11/2005 | Edwards et al. |

FOREIGN PATENT DOCUMENTS

WO              9104315          4/1991

OTHER PUBLICATIONS

Roda J.M. et al. Prevention of cerebral ischemic reperfusion injury by intra-arterial administration of superoxide dismutase in the rat, Neurological Research, 1991, vol. 13, No. 3, pp. 160-163.*

Warner D.S. et al. Review—Oxidants, antioxidants and the ischemic brain, The Journal of Experimental Biology, 2004, vol. 207, pp. 3221-3231.*
Kreuter J. et al. Apolipoprotein-mediated transport of nanoparticle-bound drugs across the blood-brain barrier, Journal of Drug Targeting, 2002, vol. 10, No. 4, pp. 317-325.*
S. Blum et al., "A Cell-Permeable Phospholipase Cyl-Binding Peptide Transduces Neurons and Impairs Long-Term Spatial Memory", Learning & Memory, 11: 239-243 (2004).
H. Chung et al., "Dendritic Oligoguanidines as Intracellular Translocators", Biopolymers, 76: 83-96 (2004).
S. Demirkaya et al., "Malondialdehyde, glutathione peroxidase and superoxide dismutase in peripheral blood erythrocytes of patients with acute cerebral ischemia", European Journal of Neurology, 8: 43-51 (2001).
S. Deshayes et al., "Insight into the Mechanism of Internalization of the Cell-Penetrating Carrier Peptide Pep-1 through Conformational Analysis", Biochemistry, 43: 1449-1457 (2004).
U. Dirnagl et al., "Global Cerebral Ischemia in the Rat: Online Monitoring of Oxygen Free Radical Production Using Chemiluminescence In Vivo", J. Cerebral Blood Flow and Metabolism, 15: 929-940 (1995).
F. E. Rey et al., "Novel Competitive Inhibitor of NAD(P)H Oxidase Assembly Attenuates Vascular O2- and Systolic Blood Pressure in Mice", Circ. Res., 89: 408-414 (2001).
K. Faulkner et al., "Stable Mn(III) Porphyrins Mimic Superoxide Dismutase in Vitro and Sugstitute for it In Vivo", J. Biol. Chem., 269: 23471-23476 (1994).
H. Hashida et al., "Fusion of HIV-1 Tat protein transduction domain to poly-lysine as a new DNA delivery tool", British Journal of Cancer, 90: 1252-1258 (2004).
D. Hermann et al., "Adenovirus-Mediated GDNF and CNTF Pretreatment Protects against Striatal Injury Following Transient Middle Cerebral Artery Occlusion in Mice", Neurobiology of Disease, 8: 655-666 (2001).
S. Futaki et al., "Arginine-rich peptides: potential for intracellular delivery of macromolecules and the mystery of the translocation of mechanisms", Intl. J. Pharm., 245: 1-7 (2002). R. Hata et al., "Evolution of Brain Infarction After Transient Focal Cerebral Ischemia in Mice", J. Cereb. Blood Flow Metabl., 20: 937-946 (2000).
H. Imai et al., "Ebselen Protects Both Gray and White Matter in a Rodent Model of Focal Cerebral Ischemia", Stroke, 32: 2149-2154 (2002).
J. Kreuter, "Nanoparticulate systems for brain delivery of drugs", Adv. Drug Deliv. Rev., 47: 65-81 (2001).
V. Labhasetwar et al., "Arterial Uptake of Biodegradable Nanoparticles: Effect of Surface Modifications", J. Pharm. Sci., 87: 1229-1234 (1998).
E. Kumura et al., "Generation of nitric oxide and superoxide during reperfusion after focal cerebral ischemia in rats", Am. J. Physiol., 270: C748-C752 (1996).
M. Lewin et al., "Tat peptide-derivatized magnetic nanoparticles allow in vivo tracking and recovery of progenitor cells", Nat. Biotechnol., 18: 410-414 (2000).
C. Lim et al., "Transferrin-Oligomers as Potential Carriers in Anticancer Drug Delivery", Pharm. Res., 21(11): 1985-1992 (2004).

(Continued)

*Primary Examiner* — Jon P Weber
*Assistant Examiner* — Satyendra Singh
(74) *Attorney, Agent, or Firm* — Patrick J. Hagan; Dann, Dorfman, Herrell and Skillman, PC

(57) ABSTRACT

The present invention relates to a method for inhibiting reperfusion injury in the brain. The method involve injecting via the carotid artery or jugular vein an antioxidant-loaded nanoparticle. A nanoparticle formulation containing an inert plasticizer is also provided for sustained release of an active agent.

9 Claims, 1 Drawing Sheet

OTHER PUBLICATIONS

M. May et al., "Selective Inhibition of NF-Kb Activation by a Peptide That Blocks the Interaction of NEMO with the IKB Kinase Complex", Science, 289: 1550-1554 (2000).

J. Panyam et al., "Fluorescence and electron microscopy probes for cellular and tissue uptake of poly(D,L-lactide-co-glycolide) nanoparticles", Int. J. Pharm., 262: 1-11 (2003).

T. Mori et al., "Intraluminal increase of superoxide anion following transient focal cerebral ischemia in rats", Brain Res., 826: 350-357 (1999).

S. Sahoo et al., "Efficacy of Transferrin-Conjugated Paclitaxel-Loaded Nanoparticles in a Murine Model of Prostate Cancer", Int. J. Cancer, 112: 335-340 (2004).

J. Wadia et al., "Transducible TAT-HA fusogenic peptide enhances escape of TAT-fusion proteins after lipid raft macropinocytosis", Nat. Med., 10: 310-331 (2004).

L. Ste-Marie et al., "Hydroxyl Radical Production in the Cortex and Striatum in a Rat Model of Focal Cerebral Ischemia", Can. J. Neurol. Sci., 27: 152-159 (2000).

F. Veronese et al., "Polyethylene glycol-superoxide dismutase, a conjugate in search of exploitation", Adv. Drug Deliv. Rev., 54: 587-606 (2002).

F. Wang et al., Doxorubicin-Gallium-Transferrin Conjugate Overcomes Multidrug Resistance: Evidence for Drug Accumulation in the Nucleus of Drug Resistant MCF-7/ADR Cells, Anticancer Res., 20: 799-808 (2000).

Abuchowski et al., "Alteration of Immunological Properties of Bovine Serum Albumin by Covalent Attachment of Polyethylene Glycol", J. Biol. Chem., 252(11): 3578-3581 (1977).

Baker et al., "Synthetic Combined Superoxide Dismutase/Catalase Mimetics are Protective as a Delayed Treatemnt in a Rat Stroke Model: A Key Role for Reactive Oxygen Species in Ischemic Brain Injury", Journal of Pharmacology and Experimental Therapeutics, 284(1): 215-221 (1998).

Denicourt et al., "Protein transduction technology offers novel therapeutic approach for brain ischemia", TRENDS in Pharmacological Sciences, 24(5): 216-218 (2003).

Gilgun-Sherki et al., "Antioxidant Therapy in Acute Central Nervous System Injury: Current State", Pharmacological Reviews, 54(2): 271-284 (2002).

Itoh et al., "Utility of an elevated plus-maze for the evaluation of memory in mice: effects of nootropics, scopolamine and electroconvulsive shock", Psychopharmacology, 101: 27-33 (1990).

Monfardini et al., "Stabilization of Substances in Circulation", Bioconjugate Chem., 9: 418-450 (1998).

Song et al., "Controlled release of U-86983 from double-layer biodegradable matrices: effect of additives on release mechanism and kinetics", Journal of Controlled Release, 45: 177-192 (1997).

Umemura et al., "Effect of 21-aminosteroid lipid peroxidation inhibitor, U74006F, in the rate middle cerebral artery occlusion model", European Journal of Pharmacology, 251: 69-74 (1994).

Watanbe et al., "Protective Effects of MCI-186 on Cerebral Ischemia: Possible Involvement of Free Radical Scavenging and Antioxidant Actions", Journal of Pharmacology and Experimental Therapeutics, 268(3): 1597-1604 (1994).

The terms "inert" and "plasticizer"—Merriam-Webster Online Dictionary, at the web: http://www.m-w.com, pp. 1-2, accessed on Nov. 22, 2006.

Chavez, F. et al., Release of lipophilic substances from polymeric nanocapsules, Revista de la Sociedad Quimica de Mexico, 46(4): 349-356 (2002).

Hillery, A.M. et al., Co-polymerised peptide particles (CPP) I: synthesis, characterisation and in vitro studies on a novel oral nanoparticle delivery system, Journal of Controlled Release, 41: 271-281 (1996).

Torchilin, P. et al., TAT peptide on the surface of liposomes affords their efficient intracellular delivery even at low temperature and in the presence of metabolic inhibitors, PNAS, 98(15): 8786-8791 (2001).

R. J. Christie, R. J., "Design and Synthesis of a New Polymer Drug Delivery Conjugate", Biomed. Sci. Instrum., 40: 136-141 (2004).

J. Davda, "Characterization of nanoparticle uptake by endothelial cells", Int. J. Pharm., 233: 51-59 (2002).

J. Koizumi et al., "Experimental studies of ischemic brain edema", Jpn. J. Stroke, 8: 1-8 (1986) [English Abstract].

M. Desai et al., "Gastrointestinal Uptake of Biodegradable Microparticles: Effect of Particle Size", Pharm. Res., 13 (12): 1838-45 (1996).

I. Fridovich, "Superoxide Radical: An Endogenous Toxicant", Ann. Rev. Pharmacol. Toxicol., 23: 239-57 (1983).

N. Grubor et al., "Novel biosensor chip of simultaneous detection of DNA-carcinogen adducts with low-temperature fluorescence", Biosensors and Bioelectronics, 19: 547-556 (2004).

L. Guzman et al., "Local Intraluminal Infusion of Biodegradable Polymeric Nanoparticles", Circulation, 94(6) 1441-1448 (1996).

T. Jain et al., "Iron Oxide Nanoparticles for Sustained Delivery of Anticancer Agents", Molecular Pharmaceutics, 2(3): 194-205 (2005).

B. Juurlink et al., "Mechanisms that Result in Damage During and Following Cerebral Ischemia", 21(2): 121-128 (1997).

S. Love, "Oxidative Stress in Brain Ischemia", Brain Pathology, 9: 119-131 (1999).

J. Panyam et al., "Rapid endo-lysosomal escape of poly(DL-lactide-co-glycolide) nanoparticles: implications for drug and gene delivery", FASEB J., 16(10): 1217-26 (2002).

J. Panyam et al., "Efficiency of Dispatch and Infiltrator Cardiac Infusion Catheters in Arterial Localization of Nanoparticles in a Porcine Coronary Model of Restenosis", Journal of Drug Targeting, 10(6): 515-523 (2002).

J. Panyam et al., "Biodegradable nanoparticles for drug and gene delivery to cells and tissue", Advanced Drug Delivery Reviews, 55: 329-347 (2003).

J. Panyam et al., "Polymer degradation and in vitro release of a model protein from poly(D,L-lactide-co-glycolide) nano- and microparticles", Journal of Controlled Release, 92: 173-187 (2003).

J. Panyam et al., "Solid-State Solubility Influences Encapsulation and Release of Hydrophobic Drugs from PLGA/PLA Nanoparticles", J. Pharm. Sci., 93(7): 1804-14 (2004).

J. Panyam et al., "Sustained Cytoplasmic Delivery of Drugs with Intracellular Receptors Using Biodegradable Nanoparticles", Mol. Pharm., 1(1): 77-84 (2003).

J. Panyam et al., "Targeting Intracellular Targets", Current Drug Delivery, 1: 235-247 (2004).

S. Prabha et al., "Size-dependency of nanoparticle-mediated gene transfection: studies with fractionated nanoparticles", Int. J. Pharm., 244: 105-115 (2002).

S. Prabha et al., "Nanoparticle-Mediated Wild-Type p53 Gene Delivery Results in Sustained Antiproliferative Activity in Breast Cancer Cells", Mol. Pharm., 1(3): 211-219 (2004).

S. Prabha et al., "Critical Determinants in PLGA/PLA Nanoparticle-Medicated Gene Expression", Pharm. Res., 21: 354-364 (2004).

M. Qaddoumi et al., "Clathrin and caveolin-1 expression in primary pigmented rabbit conjunctival epithelial cells: Role in PLGA nanoparticle endocytosis", Molecular Vision: 9: 559-68 (2003).

M. Qaddoumi et al., "The Characteristics and Mechanisms of Uptake of PLGA Nanoparticles in Rabbit Conjunctival Epithelial Cell Layers"., Pharm. Res., 21(4): 641-648 (2004).

R. J. Raghuvanshi et al., "Enhanced immune response with a combination f alum and biodegradable nanoparticles containing tetanus toxoid", J. Mlcroencapsulation, 18(6): 723-732 (2001).

S. Sahoo et al., "Residual polyvinyl alcohol associated with poly (D.K-lactide-co-glycolide) nanoparticles affects their physical properties and cellular uptake", J. Control. Release, 82: 105-114 (2002).

S. Sahoo et al., "Enhanced Antiproliferative Activity of Transferrin-Conjugated Paclitaxel-Loaded Nanoparticles is Mediated via Sustained Intracellular Drug Retention", Mol. Pharm., 2: 373-383 (2005).

C. Song et al., "Arterial uptake of biodegradable nanoparticles for intravascular local drug delivery: Results with an acute dog model", J. Control. Release, 54: 201-211 (1998).

R. Swanson et al., "A Semiautomated Method for Measuring Brain Infarct Volume", J. Cereb. Blood Flow Metab., 10: 290-293 (1990).

J. Wadia et al., "Protein transduction technology", Curr. Opin. Biotechnol., 13: 52-56 (2002).

J. Panyam et al., "Dynamics of Endocytosis and Exocytosis of Poly(D,L-Lactide-co-Glycolide) Nanoparticles in Vascular Smooth Muscle Cells", Pharm. Res., 20(2): 212-220 (2003).

* cited by examiner

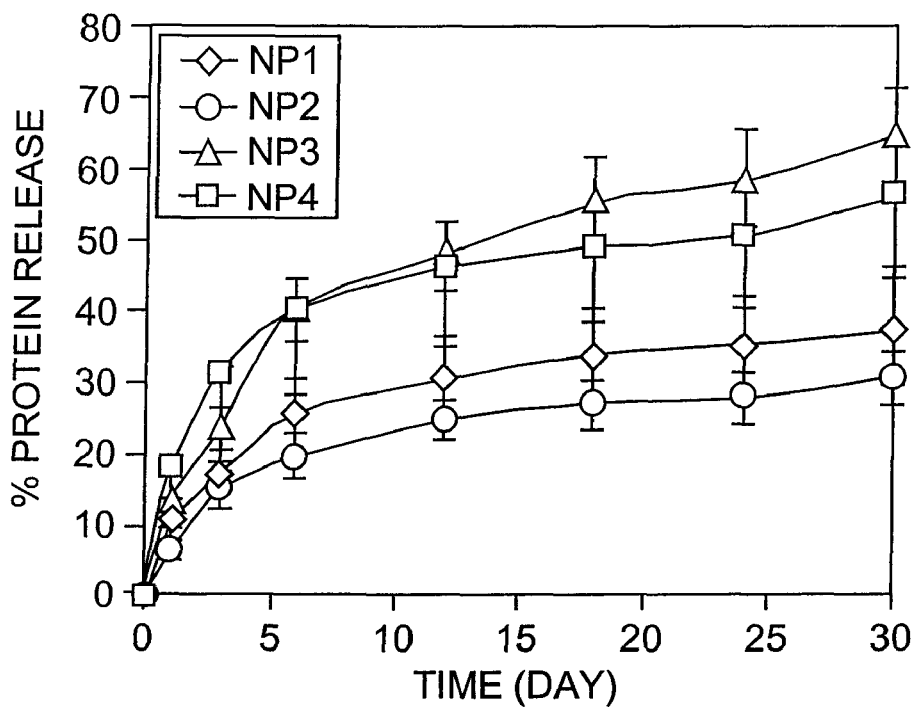
*FIG. 1*
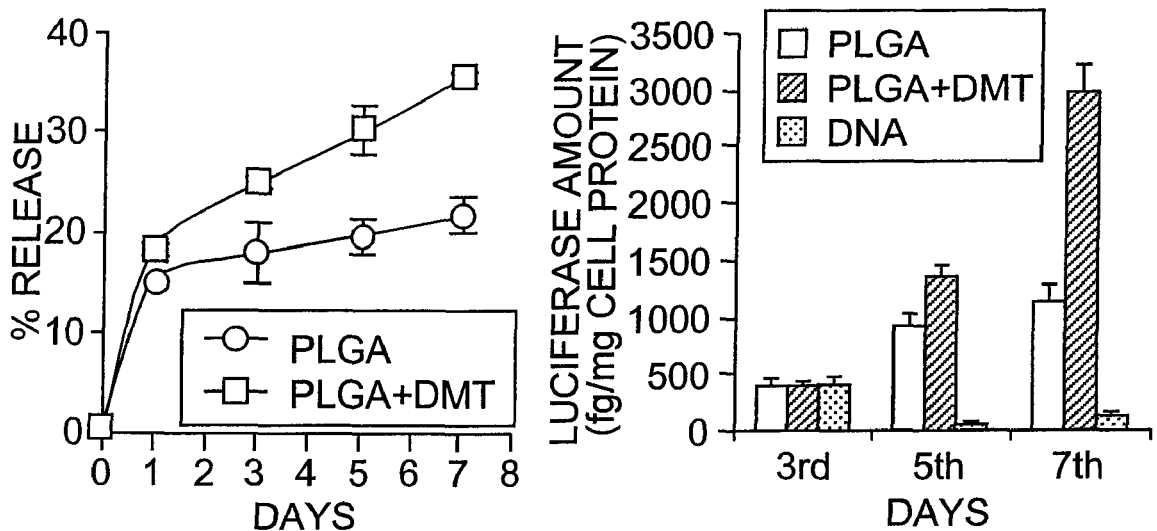
*FIG. 2A*  *FIG. 2B*

METHOD FOR INHIBITING REPERFUSION INJURY IN THE BRAIN

CROSS-REFERENCE TO RELATED APPLICATIONS

This application is a division of U.S. patent application Ser. No. 10/955,739, filed Sep. 30, 2004, which issued on Feb. 19, 2008 as U.S. Pat. 7,332,159. The entire disclosure of the aforesaid application is incorporated by reference in the present application.

BACKGROUND OF THE INVENTION

Stroke is a sudden loss of brain function resulting from interference with the blood supply to the central nervous system leading to cerebral ischemia. Many factors play a role in the development of brain damage after ischemia. Among these factors, oxidative stress has been shown to play a central role in cerebral ischemia. Oxidative stress is often initiated and propagated by overproduction of $O_2^-$ and $H_2O_2$ and their conversion to potent oxidants, such as hydroxyl radical and perioxynitrate. In general, free radical production is low, and the organism can neutralize or metabolize the toxic effects by free radical scavengers such as super oxide dismutase (SOD) and catalase (Fridovich (1983) *Annu. Rev. Pharmacol. Toxicol.* 23:239-57). Nevertheless, under some pathophysiological conditions, there is oxygen radical accumulation that impairs the cells, such as free radical accumulation during cerebral ischemia (Ste-Marie, et al. (2000) *Can. J. Neurol. Sci.* 27:152-9; Mori, et al. (1999) *Brain Res.* 816:350-7). Furthermore, the burst of free radical production has been demonstrated at the onset of reperfusion after cerebral ischemia (Dirnagl, et al. (1995) *J. Cereb. Blood Flow Metab.* 15:929-40; Kumura, et al. (1996) *Am. J. Physiol.* 270:C748-52). The brain is very susceptible to oxidative stress-induced damage because it is rich in polyunsaturated fatty acids and relatively low levels of endogenous antioxidant enzymes in neuronal tissue to neutralize the effect of free radicals (Juurlink and Sweeney (1997) *Neurosci. Biobehav. Rev.* 21:121-8). It has been demonstrated that free radicals and related reactive oxygen species mediate much of the damage that occurs after transient brain ischemia (Love (1999) *Brain Pathol.* 9:119-31). Moreover, SOD and glutathione peroxidase activities are significantly lower in stroke patients compared to control subjects, suggesting a significant correlation with infarct size, initial stroke severity and poor short-term prognosis (Demirkaya, et al. (2001) *Eur. J. Neurol.* 8:43-51). These data suggest that superoxide anion, $O_2^-$, hydrogen peroxide, and perioxynitrite are among the key reactive oxygen species implicated in ischemic injury.

Natural scavenger enzymes SOD and catalase are characterized by a very high efficiency and great stability toward oxidants. Both enzymes have been used in their native form to prevent oxidative damage but they have been found to be effective only following repeated doses or when administered locally or in isolated tissues or cells. Further, targeting and unsatisfactory pharmacokinetics have limited the use of these enzymes in methods of treatment (Abuchowski, et al. (1977) *J. Biol. Chem.* 252:3578-81; Monfardini and Veronese (1998) *Bioconjug. Chem.* 9:418-50).

As an alternative, several synthetic, free radical scavengers have been evaluated in animal models of cerebral ischemia and reperfusion and have been shown to be protective (Watanabe, et al. (1994) *J. Pharmacol. Exp. Ther.* 268:1597-604; Umemura, et al. (1994) *Eur. J. Pharmacol.* 251:69-74; Baker, et al. (1998) *J. Pharmacol. Exp. Ther.* 284:215-21; Itoh, et al. (1990) *Psychopharmacology* (Berl) 101:27-33; Gilgun-Sherki, et al. (2002) *Pharmacol. Rev.* 54:271-84). While some of the antioxidant-like SOD mimetics show efficacy in animal models, poor stability of these agents and the inability to sustain their retention at target sites are still major challenges for their therapeutic use. Delivery of SOD to the brain has been attempted via the use of prodrugs or carrier systems such as antibodies, liposomes (Kreuter (2001) *Adv. Drug. Deliv. Rev.* 47:65-81), and surface modifications such as conjugation to polyethylene glycol (SOD-PEG) (Veronese, et al. (2002) *Adv. Drug Deliv. Rev.* 54:587-606); however, treatment of cerebral ischemia/reperfusion injuries has been limited due to poor cerebral cell penetration. Gene therapy is an alternative approach but the delivery of genes into brain tissues and expression of therapeutic proteins may not be available for immediate effect (Hermann, et al. (2001) *Neurobiol. Dis.* 8:655-66). Furthermore, cerebral protein synthesis is severely compromised in injured areas after focal ischemia (Hermann, et al. (2001) supra; Hata, et al. (2000) *J. Cereb. Blood Flow Metab.* 20:937-46).

U.S. Pat. No. 6,123,956 teaches methods and compositions for treating stroke and/or traumatic brain injury. The compositions taught in this reference encompass a therapeutic agent such as SOD encapsulated in a pharmaceutically acceptable polymer, e.g., polyesters such as PLA (poly(lactide)) and PLGA (poly(D,L-lactide-co-glycolide)), polyethylene glycol, poloxomers, polyanhydrides, and pluronics), wherein the therapeutic agent is present at therapeutically effective concentrations which, if injected into the cerebrospinal fluid of a subject suffering from stroke or traumatic brain injury will contribute to the amelioration of the disorder.

SUMMARY OF THE INVENTION

The present invention relates to a method for inhibiting reperfusion injury in the brain. The method involves administering an effective amount of an antioxidant, wherein said antioxidant is formulated in a nanoparticle and administered via the carotid artery or jugular vein to a subject in need of treatment, thereby inhibiting reperfusion injury in the brain of said subject. In certain embodiments, the antioxidant is an antioxidant enzyme (e.g., superoxide dismutase, catalase, glutathione peroxidase, glutathione reductase, glutathione-S-transferase hemeoxygenase, or mimetic or synthetic enzymes thereof), a small molecule antioxidant (e.g., a vitamin antioxidant, acetyl salicyclic acid, mannitol, captopril, arginine, or pyruvate) or a combination thereof. In other embodiments, the nanoparticle is composed of a biodegradable polymer such as a poly(lactide-co-glycolide), poly(lactic acid), poly (alkylene glycol), polybutylcyanoacrylate, poly(methylmethacrylate-co-methacrylic acid), poly-allylamine, polyanhydride, polyhydroxybutyric acid, or a polyorthoester or a combination thereof. In still further embodiments, the nanoparticle contains a targeting moiety or a plasticizer such as L-tartaric acid dimethyl ester, triethyl citrate, or glyceryl triacetate to facilitate sustained release of the antioxidant.

The present invention further relates to a composition for sustained release of an effective amount of an active agent. The composition contains an active agent (e.g., antioxidant, an anti-infective, an antiseptic, a steroid, a therapeutic peptide, an analgesic, an anti-inflammatory agent, an anticancer agent, a narcotic, an anesthetic, an antiangiogenic agent, a polysaccharide, a vaccine, an antigen, or a nucleic acid), at least one biodegradable polymer (e.g., a poly(lactide-co-glycolide), poly(lactic acid), poly(alkylene glycol), polybutylcyanoacrylate, poly(methylmethacrylate-co-methacrylic acid), poly-allylamine, polyanhydride, polyhydroxybutyric acid, or a polyorthoester), and an inert plasticizer (e.g., L-tartaric acid dimethyl ester, triethyl citrate, or glyceryl triacetate). In particular embodiments, the nanoparticle composition further contains a targeting moiety.

A method for effecting a sustained release of an effective amount of an active agent using a nanoparticle containing an active agent, at least one biodegradable polymer and an inert plasticizer is also provided.

BRIEF DESCRIPTION OF THE DRAWINGS

FIG. 1 shows protein release of from nanoparticles containing dimethyl tartrate (DMT). Release of bovine serum albumin (BSA) was determined in a double diffusion chamber separated by a permeable membrane which was permeable to BSA but not nanoparticles. A suspension of nanoparticles (5 mg/mL, 2.5 mL) was filled in the donor chamber and phosphate-buffered saline (PBS) (154 mM, pH 7.4, 37° C.) in the receiver chamber. Samples from the receiver chamber were completely removed and replaced with fresh buffer. The protein levels in the released samples were analyzed by BCA protein assay. NP1, 90.0 mg polymer/0.0 mg DMT (0% DMT); NP2, 85.5 mg polymer/4.5 mg DMT (5% DMT); NP3, 81.5 mg polymer/9.0 mg DMT (10% DMT); NP4, 63.0 mg polymer/27.0 mg DMT (30% DMT).

FIG. 2A shows that the addition of DMT to PLGA nanoparticles facilitates the release of DNA (PLGA 50:50, 143 kDa, 2% weight/volume PVA as an emulsifier). Nanoparticles were suspended in Tris-EDTA buffer and incubated at 37° C. The release DNA was separated by centrifugation and quantitated using Picogreen® (Promega, Madison, Wis.).

FIG. 2B shows the level of transfection of nucleic acid sequences encoding luciferase when encapsulated in nanoparticles containing or lacking DMT. A single dose of nanoparticles (10 µg DNA) was used for transfection of MCF-7 cells. The medium in the wells was changed on day 2 and 4 after transfection with no addition of new nanoparticles. Luciferase levels were measured on day 3, 5, and 7 after transfection.

DETAILED DESCRIPTION OF THE INVENTION

The present invention relates to a method for inhibiting reperfusion injury in the brain using a highly effective course of therapy which combines an antioxidant formulated into a nanoparticle and injection of the nanoparticle formulation via the carotid artery or jugular vein. Using this protocol, it has now been shown that the nanoparticles can cross the blood brain barrier and inhibit ischemia in the brain. It has further been demonstrated that when the nanoparticle formulation contains an inert plasticizer such as dimethyl tartrate (DMT), sustained release of the active agent can be achieved.

As it pertains to the present disclosure, ischemia is used in the classical sense to refer to the condition suffered by tissues or organs when deprived of blood flow; reduced blood flow results in an inadequate supply of nutrients and oxygen in the tissues or organs. Reperfusion injury refers to the tissue damage inflicted when blood flow is restored after an ischemic period of more than about ten minutes.

Antioxidants which can be formulated in a nanoparticle of the present invention to inhibit reperfusion injury include antioxidant enzymes, small molecule antioxidants, or combinations thereof. Antioxidants are substances which inhibit oxidation or suppress reactions promoted by reactive oxygen species such as oxygen itself, oxygen free radicals, or peroxides. Antioxidants can be absorbed into the cell membrane to neutralize oxygen radicals and thereby protect the membrane.

As used herein, antioxidant enzymes are generally proteins, or their fragments, that scavenge oxygen free radicals or $H_2O_2$ (hydrogen peroxide). Suitable antioxidant enzymes include, but are not limited to superoxide dismutase, catalase, glutathione peroxidase, glutathione reductase, glutathione-S-transferase or hemeoxygenase, or mimetic or synthetic enzymes thereof. See, U.S. Pat. No. 5,994,339 for mimetic enzymes.

Small molecule antioxidants include scavengers of $.O_2^-$ (superoxide), $.OH$ (hydroxyl) or NO (nitric oxide) radicals (e.g., acetyl salicylic acid, a scavenger of $.O_2^-$; mannitol or captopril which are scavengers of $.OH$); molecules that inhibit the generation of these radicals (e.g., arginine derivatives, inhibitors of nitric oxide synthase which produce NO; pyruvate which attenuates the rate of $H_2O_2$-induced generation of reactive oxygen species); or vitamin antioxidants. Vitamin antioxidants include lycopene; lutein; xeaxanthine; all forms of Vitamin A including retinal and 3,4-didehydroretinal; all forms of carotene (e.g., alpha-carotene, beta-carotene, gamma-carotene, delta-carotene); all forms of Vitamin C (e.g., D-ascorbic acid, L-ascorbic acid); all forms of Vitamin E such as tocopherol (e.g., alpha-tocopherol, beta-tocopherol, gamma-tocopherol, delta-tocopherol), tocoquinone, tocotrienol, and Vitamin E esters which readily undergo hydrolysis to Vitamin E such as Vitamin E acetate and Vitamin E succinate, and pharmaceutically acceptable Vitamin E salts such as Vitamin E phosphate; prodrugs of Vitamin A, carotene, Vitamin C, and Vitamin E; pharmaceutically acceptable salts of Vitamin A, carotene, Vitamin C, and Vitamin E, and the like, and mixtures thereof. Analogues of Vitamin E such as TROLOX®, a compound which is more hydrosoluble than natural forms of Vitamin E and which could reach intracellular sites more rapidly, is also contemplated.

Antioxidants for use in the formulations of the present invention can be isolated from a natural source or wholly or partially synthetically- or recombinantly-produced. Methods for isolating or producing antioxidants or antioxidant extracts are well-established in the art, see, e.g., U.S. Pat. Nos. 6,737,552; 6,660,320; 6,656,358; 6,653,530; 6,623,743; RE38,009; U.S. Pat. Nos. 6,429,356; 6,436,362; 6,262,279; 6,410,290; 6,231,853; and 5,714,362 and WO 91/04315.

An effective amount of antioxidant present in a nanoparticle formulation of the present invention is an amount which prevents and/or reduces injury of mammalian brain tissue due to ischemic conditions. Such ischemic conditions can arise from acute head trauma, surgical occlusion of blood flow, stroke, cardiac arrest and the like. The exact amount of antioxidant will vary according to factors such as the antioxidant being used as well as the other ingredients in the composition. Typically, the amount of antioxidant can vary from about 1 unit/kg to about 30,000 units/kg of body weight or from about 500 units/kg to about 20,000 units/kg. In particular embodiments, the antioxidant is given at a dose of about 10,000 units/kg. The effectiveness of the antioxidant treatment can be determined by monitoring the mammals neurological status, infarct volume or plasma glucose levels as disclosed herein.

When the antioxidant is a mimetic, it has been demonstrated that the in vivo oxidoreductase activity of the mimetic is such that an effective dose will be low enough to avoid problems of toxicity (Faulkner, et al. (1994) *J. Biol. Chem.* 269:23471); therefore, doses that can be used include those in the range of 1 to 50 mg/kg.

As disclosed herein, it has been found that an antioxidant-containing nanoparticle formulation can exert its effect via any route of administration; however, intracarotid administration is particularly effective at delivering a therapeutic amount of the active agent to the brain. Accordingly, it is contemplated that an antioxidant-containing nanoparticle formulation of the present invention can be administered via intravenous, intracerebral, intracarotid, intramuscular or intrajugular routes, wherein intracarotid or intrajugular routes are suitable. In particular embodiments, intracarotid administration is advantageously used. The antioxidant-containing nanoparticle formulation of the present invention can be administered to a subject in need of such treatment including a subject at risk of reperfusion injury (e.g., in the case of surgery-induced ischemia) or a subject that has experienced an ischemic event (e.g., stroke) to prevent, inhibit and/or reduce reperfusion injury.

As one of skill in the art will appreciate, a nanoparticle in accordance with the methods and compositions of the present invention can be composed of a variety of injectable biodegradable polymers. Nanoparticles are said to be biodegradable if the polymer of the nanoparticle dissolves or degrades within a period that is acceptable in the desired application (usually in vivo therapy), usually less than five years, and desirably less than one year, upon exposure to a physiological solution of pH 6-8 having a temperature of between 25° C. and 37° C. As such, a nanoparticle for use in accordance with the methods and compositions of the present invention can be composed homopolymers or copolymers prepared from monomers of polymers disclosed herein, wherein the copolymer can be of diblock, triblock, or multiblock structure. Suitable polymers include, but are not limited to, poly(lactide-co-glycolides), poly(lactic acid), poly(alkylene glycol), polybutylcyanoacrylate, poly(methylmethacrylate-co-methacrylic acid), poly-allylamine, polyanhydride, polyhydroxybutyric acid, or polyorthoesters and the like. In particular embodiments, a nanoparticle is composed of a copolymer of a poly(lactic acid) and a poly(lactide-co-glycolide). Particular combinations and ratios of polymers are well-known to the skilled artisan and any suitable-combination can be used in the nanoparticle formulations of the present invention. Generally, the resulting nanoparticle typically ranges in size from between 1 nm and 1000 nm, or more desirably between 1 nm and 100 nm.

A nanoparticle of the present invention can further contain a polymer that affects the charge or lipophilicity or hydrophilicity of the particle. Any biocompatible hydrophilic polymer can be used for this purpose, including but not limited to, poly(vinyl alcohol).

To further enhance delivery of a therapeutically effective amount of an active agent, a nanoparticle of the present invention can further contain a targeting moiety (e.g., a protein transduction domain). As used herein, a targeting moiety is any molecule which can be operably attached to a nanoparticle of the present invention to facilitate, enhance, or increase the transport of the nanoparticle into target tissue. Such a moiety can be a protein, peptide or small molecule. For example, a variety of protein transduction domains, including the HIV-1 Tat transcription factor, Drosophila Antennapedia transcription factor, as well as the herpes simplex virus VP22 protein have been shown to facilitate transport of proteins into the cell (Wadia and Dowdy (2002) Curr. Opin. Biotechnol. 13:52-56). Further, an arginine-rich peptide (Futaki (2002) Int. J. Pharm. 245:1-7), a polylysine peptide containing Tat PTD (Hashida, et al. (2004) Br. J. Cancer 90(6):1252-8), Pep-1 (Deshayes, et al. (2004) Biochemistry 43(6):1449-57) or an HSP70 protein or fragment thereof (WO 00/31113) is suitable for targeting a nanoparticle of the present invention. Not to be bound by theory, it is believed that such transport domains are highly basic and appear to interact strongly with the plasma membrane and subsequently enter cells via endocytosis (Wadia, et al. (2004) Nat. Med. 10:310-315). Animal model studies indicate that chimeric proteins containing a protein transduction domain fused to a full-length protein or inhibitory peptide can protect against ischemic brain injury and neuronal apoptosis; attenuate hypertension; prevent acute inflammatory responses; and regulate long-term spatial memory responses (Blum and Dash (2004) Learn. Mem. 11:239-243; May, et al. (2000) Science 289:1550-1554; Rey, et al. (2001) Circ. Res. 89:408-414; Denicourt and Dowdy (2003) Trends Pharmacol. Sci. 24:216-218).

Exemplary peptide-based targeting moieties are presented in Table 1.

TABLE 1

| SOURCE | AMINO ACID SEQUENCE | SEQ ID NO: |
|---|---|---|
| PTD-4[a] | YARAAARQARA | 1 |
| HIV TAT[a] | YGRKKRRQRRR | 2 |
| PTD-3[a] | YARKARRQARR | 3 |
| PTD-5[a] | YARAARRAARR | 4 |
| PTD-6[a] | YARAARRAARA | 5 |
| PTD-7[a] | YARRRRRRRRR | 6 |
| ANTp[b] | RQIKIWFQNRRMKWKK | 7 |
| Transportin[b] | GWTLNSAGYLLGKINLKALAALAKKIL | 8 |

[a]Ho, et al. (2001) Cancer Res. 61:474-477.
[b]Schwartz and Zhang (2000) Curr. Opin. Mol. Ther. 2:2.

Suitable small molecules targeting moieties which can be operably attached to a nanoparticle of the present invention include, but are not limited to, nonpeptidic polyguanidylated dendritic structures (Chung, et al. (2004) Biopolymers 76(1):83-96) or poly[N-(2-hydroxypropyl) methacrylamide] (Christie, et al. (2004) Biomed. Sci. Instrum. 40:136-41).

To conjugate or operably attach the targeting moiety to a nanoparticle of the present invention, standard methods such as the epoxy activation method can be employed. The nanoparticle surface is contacted with an epoxy compound (e.g., DENACOL®, Nagase America Co., CA) which reacts with the hydroxyl functional group of, e.g., the PVA associated with the nanoparticle surface. The epoxy activation of the nanoparticle creates multiple sites for reaction with a ligand and also serves as a linkage between the nanoparticle surface and the peptide to avoid steric hindrance for interaction of the peptide with the cell membrane (Labhasetwar, et al. (1998) J. Pharm. Sci. 87:1229-34). The epoxy groups can react with many functional groups including amine, hydroxyl, carboxyl, aldehyde, and amide under suitable pH and buffer conditions; therefore increasing the number of possible targeting moieties which can be employed.

A nanoparticle formulation of the present invention can further contain a plasticizer to facilitate sustained release of the encapsulated active agent by maintaining the structure of the nanoparticle. Release of molecules (e.g., proteins, DNA or oligonucleotides) from nanoparticles formulated from block copolymers is, in general, not continuous. Typically, there is an initial release followed by a very slow and insignificant release thereafter. Not to be bound by theory, it is contemplated that the release profile may be as a result of the rapid initial drop in the molecular weight of the polymer which reduces the glass transition temperature of the polymer to below body temperature (37° C.); the glass transition temperature of copolymers prior to release is above body temperature (~45 to 47° C.). Moreover, with degradation, these polymers become softer thereby closing the pores which are created during the initial release phase (due to the release of active agent from the surface). Therefore, an inert plasticizer is added to a nanoparticle formulation disclosed herein to maintain the glass transition temperature above 37° C. despite a decline in molecular weight of the polymer with time. In this manner, the pores remain open and facilitate a continuous release of the encapsulated active agent. Suitable plasticizers are generally inert and can be food/medical grade or non-toxic plasticizers including, but not limited to, triethyl citrate (e.g., CITROFLEX®, Morflex Inc., Greensboro, N.C.), glyceryl triacetate (e.g., Triacetin, Eastman Chemical Company, Kingsport, Tenn.), L-tartaric acid dimethyl ester (i.e., dimethyl tartrate, DMT) and the like. A particularly suitable plasticizer is L-tartaric acid dimethyl ester.

The amount of plasticizer employed in a nanoparticle composition can range from about 5 to 40 weight percent of the nanoparticle, more desirably from about 10 to 20 weight percent of the nanoparticle. In particular embodiments, the plasticizer encompasses about 10 weight percent of the nanoparticle composition.

By enhancing the release profile of an active agent, a plasticizer-containing nanoparticle has utility in the delivery of a variety of active agents to a variety of tissues or organs. Accordingly, the present invention further relates to a composition for sustained or continuous release of an effective amount of an active agent, wherein said composition contains an active agent, at least one biodegradable polymer, and an inert plasticizer. As used herein, controlled release, sustained release, or similar terms are used to denote a mode of active agent delivery that occurs when the active agent is released from the nanoparticle formulation at an ascertainable and controllable rate over a period of time, rather than dispersed immediately upon application or injection. Controlled or sustained release can extend for hours, days or months, and can vary as a function of numerous factors. For the composition of the present invention, the rate of release will depend on the type of the plasticizer selected and the concentration of the plasticizer in the composition. Another determinant of the rate of release is the rate of hydrolysis of the linkages between and within the polymers of the nanoparticle. Other factors determining the rate of release of an active agent from the present composition include particle size, acidity of the medium (either internal or external to the matrix) and physical and chemical properties of the active agent in the matrix.

In addition to delivery of antioxidants to the brain, a sustained release nanoparticle formulation containing a plasticizer can be used to deliver any natural or synthetic, organic or inorganic molecule or mixture thereof in an amount which is sufficient to effect prevention or treatment of a disease or condition in a subject. As used herein, an active agent includes any compound or mixture of compounds which produces a beneficial or useful result. Active agents are distinguishable from such components as vehicles, carriers, diluents, lubricants, binders and other formulating aids, and encapsulating or otherwise protective components. Examples of active agents are pharmaceutical, agricultural or cosmetic agents. Suitable pharmaceutical agents include locally or systemically acting pharmaceutically active agents which can be administered to a subject according to standard methods of delivering nanoparticles (e.g., topical, intralesional, injection, such as subcutaneous, intradermal, intramuscular, intraocular, or intra-articular injection, and the like). Examples of these agents include, but not limited to, anti-infectives (including antibiotics, antivirals, fungicides, scabicides or pediculicides), antiseptics (e.g., benzalkonium chloride, benzethonium chloride, chlorohexidine gluconate, mafenide acetate, methylbenzethonium chloride, nitrofurazone, nitromersol and the like), steroids (e.g., estrogens, progestins, androgens, adrenocorticoids, and the like), therapeutic polypeptides (e.g. insulin, erythropoietin, morphogenic proteins such as bone morphogenic protein, and the like), analgesics and anti-inflammatory agents (e.g., aspirin, ibuprofen, naproxen, ketorolac, COX-1 inhibitors, COX-2 inhibitors, and the like), cancer chemotherapeutic agents (e.g., mechliorethamine, cyclophosphamide, fluorouracil, thioguanine, carmustine, lomustine, melphalan, chlorambucil, streptozocin, methotrexate, vincristine, bleomycin, vinblastine, vindesine, dactinomycin, daunorubicin, doxorubicin, tamoxifen, and the like), narcotics (e.g., morphine, meperidine, codeine, and the like), local anesthetics (e.g., the amide- or anilide-type local anesthetics such as bupivacaine, dibucaine, mepivacaine, procaine, lidocaine, tetracaine, and the like), antiangiogenic agents (e.g., combrestatin, contortrostatin, anti-VEGF, and the like), polysaccharides, vaccines, antigens, nucleic acids (e.g., DNA and other polynucleotides, antisense oligonucleotides, and the like), etc.

As will be appreciated by the skilled artisan, the nanoparticle compositions of the present invention can further contain additional fillers, excipients, binders and the like depending on, e.g., the route of administration and the active agents used. A generally recognized compendium of such ingredients and methods for using the same is Remington: The Science and Practice of Pharmacy, Alfonso R. Gennaro, editor, 20th ed. Lippingcott Williams & Wilkins: Philadelphia, Pa., 2000.

By way of illustration, the compositions and methods of the present invention were employed in a rat model of reperfusion injury wherein delivery of the active agent was targeted to the brain. Localization of DMT-containing nanoparticles in the brain, when administered via different routes, was demonstrated using a formulation of nanoparticles loaded with the fluorescent dye 6-coumarin (0.05%). In this manner, the dye acts as a marker and can be used to quantitatively determine the uptake of nanoparticles in cells or tissues (Panyam, et al. (2003) *Int. J. Pharm.* 262:1-11). Formulations containing rat serum albumin and 50 µg of dye were prepared as disclosed herein for BSA. The dye was dissolved in the polymer solution prior to emulsification. A suspension of nanoparticles in saline was infused (a 35 mg/kg dose dispersed in 500 µL of saline using water bath sonication) at the rate of 200 µL/minute either via the intracarotid, intrajugular vein, or intravenous route. These studies were carried out in animals in which no cerebral ischemia was induced. One hour after nanoparticle administration, rats were euthanized, transcardially perfused with 200 mL of heparanized saline, and the brains collected for quantitative analysis of nanoparticle uptake. To analyze nanoparticle levels, brain samples were homogenized in 100 µL saline, lyophilized for 48 hours, and the dry weight was measured. To extract the dye from the nanoparticles localized in the tissue, 10 mL of methanol was added to each sample and incubated on an orbital shaker for 48 hours. After 48 hours, one milliliter of solution was taken from the tissue bottle and centrifuged at 14,000 rpm for 15 minutes. The supernatant was collected and the dye concentration in the sample was determined using high performance liquid chromatography (HPLC). A standard plot using nanoparticles was prepared using identical conditions to determine the amount of nanoparticles localized in the brain.

The results of this analysis indicated that comparable uptake of nanoparticles into the brain could be achieved via intravenous or intrajugular administration. With intracarotid administration, the nanoparticle brain levels were 20-fold higher (~600 μg/gram of tissue) than that with intravenous or intrajugular administration. The brain uptake of DMT-containing nanoparticles via intracarotid route was about 1.7% of the total dose that was administered, indicating that a significant amount of DMT-containing nanoparticles can be localized to the brain when administered via the intracarotid artery. Further, total brain uptake was independent of the condition of the brain as uptake of dye-loaded nanoparticles following ischemia was found to be comparable to that in the normal brain via intravenous route of administration.

To demonstrate the effect of SOD on inhibition of ischemia in the brain, saline (n=4), SOD in solution (10,000 U/kg, n=2), low dose SOD-containing nanoparticles (10,000 U/kg, n=4) or high dose SOD-containing nanoparticles (20,000 U/kg, n=5) were administered to rats via intracarotid route at the time of reperfusion. The nanoparticles employed (40 mg/kg) were dispersed in 500 μL of saline and infused via the carotid artery at the rate of 100 μL/minute. It was found that SOD in solution had no effect on infarct volume. Conversely, animals treated with SOD-containing nanoparticles exhibited a significant 60% reduction in total infarct volume (low dose, ~180 mm$^3$; high dose, ~130 mm$^3$) as compared to that of saline control (~345 mm$^3$).

Behavioral data demonstrated that the motor and somatosensory functions were impaired by the ischemic insult. Neurological deficit scores were significantly higher for animals administered saline control (deficit score≈11) and SOD in solution (deficit score≈12) as compared to that animals administered SOD-containing nanoparticles (deficit score≈2-3). As animals receiving control nanoparticles demonstrated similar results as the saline control group, these data demonstrate that the beneficial outcome imparted by SOD-containing nanoparticles was due to the sustained delivery of SOD to the brain by the nanoparticles.

The integrity of the blood-brain barrier was also assessed in animals administered SOD-containing nanoparticles. Cerebral ischemia was developed by occlusion of the middle cerebral artery for 60 minutes. A solution of Evans blue dye (0.3 mL of 4% solution; Sigma, St. Louis, Mo.) was injected through the tail vein of the animals and immediately a suspension of SOD-containing nanoparticles (SOD dose=20,000 U/kg) was infused through the carotid artery prior to reperfusion. Six hours after reperfusion, rats were sacrificed, transcardially perfused to remove blood and the brains were collected and photographed. A saline control animal showed intense coloration of the brain due to extravasation of the dye into the brain, indicating disruption of the blood-brain barrier. In contrast, brains of animals infused with SOD-containing nanoparticles showed significantly lower extravasation of the dye. It is believed that the SOD-containing nanoparticles protected the endothelium thereby maintaining the integrity of the blood-brain barrier and preventing damage to the brain.

The invention is described in greater detail by the following non-limiting examples.

EXAMPLE 1

Formulation and Characterization of Nanoparticles

PLGA (90 mg; 50:50, inherent viscosity 1.31; Birmingham Polymers, Inc., Birmingham, Ala.) was dissolved in 3 mL of chloroform. Dimethyl tartrate (DMT or tartaric acid dimethyl ester; density 1.238 g/mL; Sigma, St. Louis, Mo.) was dissolved in the polymer solution. Protein (30 mg of BSA) was dissolved in 300 μL of water. The protein solution was emulsified into the PLGA solution by vortexing for 1 minute and then sonicating for 2 minutes at 55 Watts energy output using a probe sonicator (XL 2015 Sonicator® ultrasonic processor, Misonix, Inc., Farmingdale, N.Y.).

The resulting primary emulsion was further emulsified into 12 mL of 2% PVA solution (PVA average molecular weight 30,000-70,000) by vortexing followed by sonicating for 2 minutes at 55 Watts. PVA solution was filtered through a 0.22 micron syringe filter and saturated with chloroform prior to use. A few drops of chloroform were added at a time into the PVA solution, shaken and the supernatant was used for the formulation.

The emulsion was stirred overnight on a stir plate at room temperature followed by desiccation under vacuum for 1 hour. Nanoparticles thus formed were separated by centrifugation at 30,000 rpm for 30 minutes at 4° C. (Beckman OPTIMA™ LE-80K, Beckman Instruments, Inc., Palo Alto, Calif.). Pelleted nanoparticles were resuspended in water and centrifuged again as indicated above. The supernatant was collected and the process was repeated one additional time to remove unencapsulated protein and emulsifier. The supernatants were collected and analyzed for protein levels to determine the amount of protein not encapsulated in the nanoparticles. Protein levels were determined using BIORAD® assay kit.

Nanoparticles were suspended in water by sonication as above. The suspension was lyophilized for 48 hours (VirTis Company, Inc. freeze dryer, Gardiner, N.Y.).

The diameter of the nanoparticles was obtained with photon correlation spectroscopy (PCS) using quasi elastic light scattering equipment (ZETAPLUS™, zeta potential analyzer, Brookhaven Instruments Corp., Holtsville, N.Y.) and ZETAPLUS™ particle sizing software (version 2.07).

To evaluate the release of nanoparticles containing DMT, DMT was dissolved in the polymer solution, at various ratios, prior to emulsification of the model protein bovine serum albumin (BSA) or model DNA sequence encoding luciferase.

It was found that with increasing concentrations of DMT, entrapment efficiency of protein in the nanoparticles was reduced; however, the particle size and polydispersity of nanoparticles was not significantly affected (Table 2).

TABLE 2

| Polymer/DMT (mg) (% of DMT) | Protein Loading % | Particle Size (nm) | Polydispersity Index |
|---|---|---|---|
| 90.0/0.0 (0%) | 18.3 | 396 | 0.12 |
| 85.5/4.5 (5%) | 15.8 | 404 | 0.13 |
| 81.5/9.0 (10%) | 11.2 | 350 | 0.15 |
| 63.0/27.0 (30%) | 10.8 | 326 | 0.14 |

*Mean hydrodynamic diameter measured by photon correlation spectroscopy in 0.001 M HEPES buffer pH 7.0.

The release of BSA from nanoparticles containing 10% DMT was greater than that from nanoparticles lacking DMT (70% vs 30% in 30 days) (FIG. 1). Further, the protein released from nanoparticles containing DMT had significantly reduced aggregation as compared to that released from nanoparticles lacking DMT.

Likewise, the release of DNA from nanoparticles containing 10% DMT was enhanced compared to nanoparticles lacking DMT (FIG. 2A) and gene transfection was also facilitated (FIG. 2B). Addition of DMT at 10% concentration did not alter the DNA loading capacity or particle size of the nanoparticles compared to nanoparticles lacking DMT.

EXAMPLE 2

SOD-Containing Nanoparticles

SOD-containing nanoparticles with DMT were formulated as described for BSA. In general, 10% DMT was used in the nanoparticle formulations. In addition to SOD, rat serum albumin (RSA) was included (in the place of BSA) and the SOD was dissolved into the RSA solution. Two formulations of SOD-containing nanoparticles were prepared: low dose SOD-containing nanoparticles (~10,000 Units SOD dose), 6 mg SOD (1 mg SOD=4,750 Units) and 24 mg RSA; and high dose SOD-containing nanoparticles (~20,000 Units SOD dose), 12 mg SOD and 18 mg RSA.

SOD loading in nanoparticles was determined by analyzing the amount of SOD that did not get encapsulated. For this purpose, the washings generated during the preparation of the nanoparticles, as disclosed herein, were collected and analyzed for SOD enzyme activity using a standard SOD enzyme assay kit (Dojindo Labs, Kumamoto, Japan). SOD loading into the nanoparticles was 4.5% (weight/weight; or 215 Units SOD per milligram nanoparticles) with an encapsulation efficiency of 75% (i.e., 75% of the added protein was encapsulated into nanoparticles).

To demonstrate the sustained release nature of the nanoparticles, an in vitro release study was carried out using a double diffusion chamber separated by a hydrophilic low protein binding MILLIPORE® membrane (0.1 μm porosity). The donor side of the diffusion cell was loaded with a suspension of nanoparticles containing 5 mg of nanoparticles in 2.5 mL phosphate-buffered saline (0.15 M, pH 7.4, 1% BSA, 0.05% TWEEN™ 20, and 0.05% sodium azide at 37° C.). The receiver side contained the buffer described above without nanoparticles. The solution from the receiver chamber was completely removed at regular time intervals and analyzed for SOD levels.

The release study under in vitro conditions demonstrated sustained release of the SOD protein encapsulated in nanoparticles. As the amount of SOD protein released was determined via enzyme activity, these data indicate that the encapsulated and released SOD protein retained its enzyme activity with time (Table 3).

TABLE 3

| Time (Hours) | % SOD Released |
|---|---|
| 3 | 4.4 |
| 12 | 13 |
| 24 | 22.7 |
| 72 | 33.4 |
| 168 | 49.1 |

EXAMPLE 3

Targeting of Nanoparticles

Drug-loaded nanoparticles are surface modified with a protein transduction domain such as TAT peptide (SEQ ID NO:2) using an epoxy activation method. TAT peptide is a suitable targeting moiety as it has been effectively conjugated to proteins and liposomes (Torchilin, et al. (2001) *Proc. Natl. Acad. Sci. USA* 98:8786-91). To conjugate or link the TAT peptide to a nanoparticle, the nanoparticle surface is contacted with an epoxy compound (e.g., DENACOL®, Nagase America Co., Calif.) which reacts with the hydroxyl functional group of the PVA associated with the nanoparticle surface. In brief, 40 mg of drug-loaded nanoparticle dispersed in 4 mL borate buffer (pH 5.0) and 12 mg DENACOL® 524 (pentaepoxy) dissolved in equal volume of borate buffer is mixed and the reaction is allowed to take place for 30 minutes at 37° C. with gentle stirring in the presence of zinc tetrafluroborate acting as a catalyst. The unreacted DENACOL® is separated from the nanoparticles by ultracentrifugation followed by a single wash with borate buffer. For conjugation to the TAT peptide, the epoxy-activated drug-loaded nanoparticle is suspended in the borate buffer and mixed with a solution of TAT peptide in 4 mL of borate buffer. The reaction is allowed to take place for 30 minutes at 37° C. and the unreacted peptide is separated by ultracentrifugation with repeated washing with water.

The amount of TAT peptide can be optimized; however, a ratio of 1:10 weight/weight TAT peptide to liposomes has been used to attach approximately 100 to 500 molecules of TAT peptide per liposome particle of ~200 nm in diameter (Torchilin, et al. (2001) supra). Further, using a 40 nm diameter dextran-coated iron nanoparticle, it has been demonstrated that as few as four TAT peptide molecules per particle were effective in achieving ~200-fold greater particle uptake into hematopoietic and neural progenitor cells as compared to unmodified particles (Lewin, et al. (2000) *Nat. Biotechnol.* 18:410-4). Therefore, based on the molecular weight of TAT peptide (1560 Da), an estimated four TAT peptide molecules per particle and the number of nanoparticles having a mean diameter of 25 nm present per mg ($\sim 10^{12}$), it is contemplated that 0.156 μg of peptide per mg weight of nanoparticles is suitable.

To determine the stability of the TAT peptide-nanoparticle conjugate, nanoparticles conjugated to FITC-labeled TAT peptide are dispersed in a serum-containing medium with aliquots centrifuged at different time points so that supernatants can be measured for fluorescence which is indicative of degradation of the nanoparticle.

EXAMPLE 4

Antioxidant Neuroprotection in Ischemia/Reperfusion Injury

Surgery leading to focal cerebral ischemia was performed under ketamine (80 mg/kg) and xylazine (10 mg/kg) injected intraperitoneally and supplemented as necessary during the procedure. Focal cerebral ischemia was accomplished by means of a modification of the established intraluminal thread model (3-0 nylon monofilament suture) (Koizumi, et al. (1986) *Jpn. J. Stroke* 8:1-8). Briefly, the left common, internal, and external carotid arteries were exposed through a ventral midline neck incision. The external carotid artery and common carotid artery were ligated and a 19 to 22 mm length of poly-L-lysine-coated 3-0 nylon suture was introduced into the lumen of the internal carotid artery and was advanced to block the origin of the middle cerebral artery. After 60 minutes of ischemia, the monofilament was removed, the wound was sutured, and the animal was allowed to recover from anesthesia with free access to food and water. A subcutaneous injection of saline (2 mL) was administered to prevent post-anesthetic dehydration.

Neurological evaluations were carried out at six hours after the induction of ischemia and reperfusion and the animals were subsequently euthanized for histological analysis of the brain to determine the extent of focal ischemia. Neurological evaluations were performed according to a fourteen-point scale (Table 4).

TABLE 4

| Motor Tests | Maximum Points |
|---|---|
| Muscle Status: Hemiplegia | |
| Raising the rat by the tail | |
| Flexion of forelimb | 1 |
| Flexion of hindlimb | 1 |
| Head moving more than 100 (vertical axis) | 1 |

TABLE 4-continued

| Motor Tests | Maximum Points |
|---|---|
| Placing the rat on the floor | |
| Inability to walk straight | 1 |
| Circling toward the paretic side | 1 |
| Falling down to the paretic side | 1 |
| Abnormal movements | |
| Immobility and staring | 1 |
| Tremor (wet-dog shakers) | 1 |
| Myodystony, irritability, seizures | 1 |
| Sensory Test | |
| Visual and tactile placing | 1 |
| Proprioceptive test (deep sensory) | 1 |
| Relexes (blunt or sharp stimulation) absent of: | |
| Pinna reflex (a head shake when touching the auditory meauts) | 1 |
| Corneal reflex (an eye blink when lightly touching the cornea with cotton) | 1 |
| Startle reflex (a motor response to a brief, loud paper noise) | 1 |
| Maximum Points | 14 |

(Longa, et al. (1989) Stroke 20: 84-91; Minematsu, et al. (1992) Stroke 23: 1304-1311)

After ischemia/reperfusion and neurological score evaluation, rats were sacrificed with an overdose of sodium pentobarbitone and transcardially perfused with normal saline. Brains were carefully removed, and sectioned into six, 2 mm-thick coronial slices using rodent brain matrices (Electron Microscopy Sciences, Hatfield, Pa.). Corneal brain slices were immediately immersed into 2% 2,3,5-triphenyltetrazolium chloride (Sigma, St. Louis, Mo.) for 20 minutes at room temperature in the dark followed by fixation in a 4% paraformaldehyde overnight. Infarct volume was calculated using the indirect method, in which the infarcted area of the brain slice was first determined using the NIH Image program by subtracting the undamaged are of ipsilateral hemisphere from the total of the contralateral hemisphere (Swanson, et al. (1990) *J. Cereb. Blood Flow Metab.* 10:290-3). The infarcted area was then multiplied by section thickness (2 mm) to obtain infarct volume for that slice. Total brain infarct volume was finally obtained by summing the volumes of the series of six brain slices prepared from each animal.

EXAMPLE 5

Additional Measurements for Assessing Ischemia/Reperfusion Injury

Intra-ischemic plasmic glucose is an important determinant of infarct size (He, et al. (1993) supra). Plasma glucose levels are determined using any commercially available glucose analyzer. Arterial blood gases and pH are measured using a Radiometer blood gas analyzer (Copenhagen, Denmark).

Local cortical blood flow (LCBF) is monitored in the left hemisphere in the supply territory of the middle cerebral artery by laser Doppler flowmetry. Each animal is placed supine, and the head is firmly immobilized in a stereotaxic frame (model 900, David Kopf Instruments). Burr holes (1.5-mm diameter) are drilled 5-6 mm lateral and 1-2 mm posterior to bregma, without injury to the dura mater. The laser Doppler flow probe is carefully positioned on the craniectomy site and LCBF is continuously monitored (2-Hz sampling rate) from before the onset of ischemia, during and five minutes after reperfusion. Flow values, averaged over 30-second periods, are collected every 10 minutes, with shorter intervals immediately after induction of ischemia and reperfusion. Decreased levels of LCBF, during intraluminal filament insertion, are expressed as a percentage of baseline flow (ischemic LCBF/preischemic LCBF)×100). According to established methods (Imai, et al. (2002) *Stroke* 32:2149-54), if ischemic LCBF is not reduced with stabilization at <35% of the baseline signal, middle cerebral artery occlusion is regarded as incomplete and animal are excluded from the study.

What is claimed is:

1. A method for inhibiting reperfusion injury in the brain comprising administering an effective amount of an antioxidant, wherein said antioxidant is formulated in a biodegradable nanoparticle and administered via the carotid artery to a subject having cerebral ischemia, said nanoparticle providing sustained release of said antioxidant, thereby inhibiting reperfusion injury in the brain of said subject.

2. The method of claim 1, wherein the antioxidant comprises an antioxidant enzyme, small molecule antioxidant, or a combination thereof.

3. The method of claim 2, wherein the antioxidant enzyme comprises superoxide dismutase, catalase, glutathione peroxidase, glutathione reductase, glutathione-S-transferase hemeoxygenase, or mimetic or synthetic enzymes thereof.

4. The method of claim 2, wherein the small molecule antioxidant comprises a vitamin antioxidant, acetyl salicyclic acid, mannitol, captopril, arginine, or pyruvate.

5. The method of claim 4, wherein the vitamin antioxidant comprises lycopene, lutein, xeaxanthine, Vitamin A, carotene, Vitamin C, tocopherol, or prodrugs or pharmaceutically acceptable salts thereof.

6. The method of claim 1, wherein the nanoparticle comprises a biodegradable polymer comprising a poly(lactide-co-glycolide), poly(lactic acid), poly(alkylene glycol), polybutylcyanoacrylate, poly(methylmethacrylate-co-methacrylic acid), poly-allylamine, polyanhydride, polyhydroxybutyric acid, or a polyorthoester or a combination thereof.

7. The method of claim 1, wherein the nanoparticle further comprises a targeting moiety.

8. The method of claim 1, wherein the nanoparticle further comprises a plasticizer to facilitate sustained release of the antioxidant.

9. The method of claim 8, wherein the plasticizer comprises L-tartaric acid dimethyl ester, triethyl citrate, or glyceryl triacetate.

* * * * *

SEQUENCE LISTING

```
<160> NUMBER OF SEQ ID NOS: 8

<210> SEQ ID NO 1
<211> LENGTH: 11
<212> TYPE: PRT
<213> ORGANISM: Artificial Sequence
<220> FEATURE:
<223> OTHER INFORMATION: Synthetic peptide targeting moiety

<400> SEQUENCE: 1

Tyr Ala Arg Ala Ala Ala Arg Gln Ala Arg Ala
 1               5                  10

<210> SEQ ID NO 2
<211> LENGTH: 11
<212> TYPE: PRT
<213> ORGANISM: Artificial Sequence
<220> FEATURE:
<223> OTHER INFORMATION: Synthetic peptide targeting moiety

<400> SEQUENCE: 2

Tyr Gly Arg Lys Lys Arg Arg Gln Arg Arg Arg
 1               5                  10
```

```
<210> SEQ ID NO 3
<211> LENGTH: 11
<212> TYPE: PRT
<213> ORGANISM: Artificial Sequence
<220> FEATURE:
<223> OTHER INFORMATION: Synthetic peptide targeting moiety

<400> SEQUENCE: 3

Tyr Ala Arg Lys Ala Arg Arg Gln Ala Arg Arg
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Synthetic peptide targeting moiety

<400> SEQUENCE: 4

Tyr Ala Arg Ala Ala Arg Arg Ala Ala Arg Arg
1               5                   10

<210> SEQ ID NO 5
<211> LENGTH: 11
<212> TYPE: PRT
<213> ORGANISM: Artificial Sequence
<220> FEATURE:
<223> OTHER INFORMATION: Synthetic peptide targeting moiety

<400> SEQUENCE: 5

Tyr Ala Arg Ala Ala Arg Arg Ala Ala Arg Ala
1               5                   10

<210> SEQ ID NO 6
<211> LENGTH: 11
<212> TYPE: PRT
<213> ORGANISM: Artificial Sequence
<220> FEATURE:
<223> OTHER INFORMATION: Synthetic peptide targeting moiety

<400> SEQUENCE: 6

Tyr Ala Arg Arg Arg Arg Arg Arg Arg Arg Arg
1               5                   10

<210> SEQ ID NO 7
<211> LENGTH: 16
<212> TYPE: PRT
<213> ORGANISM: Artificial Sequence
<220> FEATURE:
<223> OTHER INFORMATION: Synthetic peptide targeting moiety

<400> SEQUENCE: 7

Arg Gln Ile Lys Ile Trp Phe Gln Asn Arg Arg Met Lys Trp Lys Lys
1               5                   10                  15

<210> SEQ ID NO 8
<211> LENGTH: 27
<212> TYPE: PRT
<213> ORGANISM: Artificial Sequence
<220> FEATURE:
<223> OTHER INFORMATION: Synthetic peptide targeting moiety

<400> SEQUENCE: 8

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25
```